United States Patent [19]
Cherukuri et al.

[11] Patent Number: 5,587,172
[45] Date of Patent: Dec. 24, 1996

[54] PROCESS FOR FORMING QUICKLY DISPERSING COMESTIBLE UNIT AND PRODUCT THEREFROM

[75] Inventors: Subraman R. Cherukuri, Towner, N.J.; Garry L. Myers; Gerald E. Battist, both of Reston, Va.; Richard C. Fuisz, Great Falls, Va.

[73] Assignee: Fuisz Technologies Ltd., Chantilly, Va.

[21] Appl. No.: 452,666

[22] Filed: May 26, 1995

Related U.S. Application Data

[60] Division of Ser. No. 259,258, Jun. 14, 1994, which is a continuation-in-part of Ser. No. 133,669, Oct. 7, 1993, and Ser. No. 119,974, Sep. 10, 1993, Pat. No. 5,518,551.

[51] Int. Cl.⁶ .................................................. A61K 9/20
[52] U.S. Cl. ..................... 424/401; 424/489; 424/499
[58] Field of Search .................................. 424/488, 401, 424/489, 38, 490, 499

[56] References Cited

U.S. PATENT DOCUMENTS

| | | | |
|---|---|---|---|
| 3,686,000 | 8/1972 | Lawrence | 99/134 R |
| 4,327,077 | 4/1982 | Puglia et al. | 424/38 |

Primary Examiner—Thurman K. Page
Assistant Examiner—Sharon Howard
Attorney, Agent, or Firm—Hoffmann & Baron

[57] ABSTRACT

The present invention is a method of preparing a comestible unit which disperses quickly in the mouth. The present invention also includes the product resulting from the method. The method includes initiating crystallization of shearform matrix and combining with an additive, either before or after initiating crystallization, to form flowable, compactible micro-particulates. The combination is then subjected to compacting to form a comestible unit having high structural integrity, good appearance, and excellent release characteristics.

23 Claims, 2 Drawing Sheets

PROCESS FOR FORMING QUICKLY DISPERSING COMESTIBLE UNIT AND PRODUCT THEREFROM

The present application is a division of Ser. No. 08/259,258, filed Jun. 24, 1994 which is a continuation-in-part application of U.S. application Ser. No. 08/133,669 filed Oct. 7, 1993 and a continuation-in-part of U.S. application Ser. No. 08/119,974 filed Sep. 10, 1993 and now U.S. Pat. No. 5,518,551. Reference is also made to co-pending commonly-owned U.S. application Ser. No. 08/259,496 filed Jun. 14, 1994, the contents of which are incorporated herein.

BACKGROUND OF THE INVENTION

The present invention relates to the art of making comestible dosage units, such as tablets, which disintegrate quickly in the mouth.

Dosage units in the form of tablets are usually prepared by compressing a formulation containing a medicinal substance or drug and other ingredients, such as excipients selected for properties which facilitate production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

The preparation of formulations for tabletting by wet granulation is the oldest method and still the most widely used. Wet granulation involves many steps, including: milling of drugs and excipients, mixing of the milled powders, preparation of binder solution, mixing of binder solution with powder mixture to form a wet mass, coarse screening of the wet mass using 6–12 mesh screens, drying of moist granules, screening of dry granules through 14–20 mesh screen, mixing of screen granules with lubricant and disintegrant, and tablet compression.

Wet granulation is an expensive process because it requires many processing steps and involves considerable material handling equipment. Consequently, the process requires both energy and substantial space which should be environmentally controlled.

Generally, free water and heat are inimical to active ingredient. Wet granulation procedures involve water and/or heat. Therefore, it is desirable to provide a method for making tablets in the substantial absence of heat and free water in order to enhance the survival of active ingredients incorporated in the tablet.

Dry granulation refers to the granulation of a powder mixture by compression without the use of heat and solvent. Dry granulation is used when wet granulation is not available because the drug is sensitive to moisture or heat.

Two methods are used for dry granulation. One method is slugging, where the powder is precompressed on a heavy-duty tablet press, and the resulting tablets or slugs are milled to yield the granulation. The other method is precompression of the powder with pressure rolls using a compactor.

Dry granulation has many disadvantages. It requires a specialized heavy-duty tablet press to form the slug; it does not permit uniform color distribution as can be achieved with wet granulation, where dye can be incorporated into the binder liquid; the pressure roll press cannot be used with insoluble drugs because this may retard the dissolution rate; and the process tends to create dust thereby increasing the potential for cross-contamination.

Direct compression tabletting has the least amount of steps. Direct compression is used in a process by which tablets are compressed directly from powder blends of the active ingredient and suitable excipients (including fillers, disintegrants, and lubricants) which are included in the mix to provide uniform flow into the die cavity and form a firm solid compression tablet. No pretreatment of the powder blends by wet or dry granulation procedures is necessary.

Although it has considerably fewer steps than either wet or dry granulation processes, direct compression also has many technological limitations. These limitations include primarily obtaining sufficient flow, and obtaining bonding of particles to form a strong compressed tablet. Low-dose drugs are difficult to blend, that is, uniform distribution of the drug is not easily attained and unblending sometimes occurs during the compression stage. High-dose drugs do not lend themselves to direct compression because of poor flowability and poor compressibility. A typical example would be some of the antacid drugs, such as aluminum hydroxide and magnesium carbonate.

When direct compression is used the choice of excipients is extremely critical. It is desirable that when using direct compression fillers and binders possess both compressibility and fluidity. In addition to compressibility failures, the process of direct compression also has disadvantages in the area of blending. Direct compression blends are subject to unblending in post blending handling steps. Differences in particle size because of differences in density between drug and excipient particles may also lead to unblending in the hopper or feedframe on the tablet press.

A disadvantage of all prior art process is the production of fines usually associated with making compression tablets. In the prior art, preparation of particles for formulation of tablets by compression results in a noticeable amount of fines, i.e., very tiny particles on the order of 150 microns and less. These fines can interfere with operation of apparatus for feeding tabletting machines as well as the operation of the tabletting machines. Often, it is necessary to conduct tablet production in a facility which is environmentally controlled to eliminate or reduce the fines. This adds to the cost of production of the tablets.

Moreover, a percentage of the non-compressed particulate is lost during production because there are fines dispersed and cannot be recaptured, and because some of the fines are not capable of being recovered for recycle.

In order to overcome the disadvantages associated with the prior art set forth above, technology has been developed by the common owner of the present application and co-pending U.S. parent application Ser. No. 194,682 filed Feb. 10, 1994. The commonly-owned case discloses a unique procedure in which compression tabletting can be simply and accurately manufactured by "fuse and compression" steps. Fusion is achieved by flash flow processing the tablet ingredients to provide shearform matrix masses which are subsequently compressed to form comestible compression units. This process includes advantages of wet and dry granulation and direct compression but does not have the disadvantages associated with these prior art procedures.

In another commonly-owned application (bearing Attorney's Docket 447-105) filed on the same date as the present application, a rapidly-dissolving unit dosage and preparation and apparatus for making same are disclosed. The method disclosed in case 447-105 includes mixing uncured shearform matrix material with an additive followed by tamping the resulting mixture to form a dosage unit. The tamped unit is subsequently cured by exposing to controlled ambient heat, moisture, and pressure.

Dr. Fuisz also has several patents which relate to other unique delivery means. For example, in U.S. Pat. No. 4,855,326, Dr. Fuisz discloses a fiber form of medicament-bearing product which can be compacted to form a sheet-like body. He cautions, however, that the compact body cannot be squeezed too much for fear of breaking the fibrous mass. There is no indication to form a compressed tablet as a medicinal dosage form.

Similarly, in U.S. Pat. No. 4,873,085 a spun fibrous cosmetic is disclosed as well as a compacted form of sugar fibers to form a sheet-like body which can be handled more readily. There is no indication to form a compressed tablet.

In U.S. Pat. No. 4,997,856, a wafer-like structure is disclosed in which a medicament is distributed on or through spun fibers which are then chopped by passing through a conventional "food grinder" (Hobart hamburger grinder). The enclosed volume of the end product is less than 30%, and preferably less than 15% of the as-spun volume of floss. There is no mention in the '856 disclosure to form a compressed tablet.

The use of compacted spun fibers in the same sense as in the patents mentioned above is also disclosed in U.S. Pat. Nos. 5,034,421 and 5,096,492. None of these disclosures suggest formation of a compressed tablet.

While the procedure described above in commonly-owned application 447-105 discloses a technique for making a rapidly dissolving dosage unit, none of the other procedures provide a technique for forming a dosage unit which quickly disintegrates in the mouth of the consumer, but which can be conveniently manufactured for shipment and sales. It is, therefore, an object of the present invention to provide another method for preparing a dosage unit which quickly disintegrates in the mouth.

Other and further objects will be realized by those skilled in the art in view of the following disclosure.

SUMMARY OF THE INVENTION

The present invention is a method of preparing a comestible unit which quickly disperses in the mouth of the consumer. The method includes initiating crystallization of shearform matrix either before or after combining the shearform matrix with an additive to form flowable, compactible micro-particulates. The combination, which includes at least partially crystallized shearform matrix, is then compacted to form the comestible unit.

Preferably, a crystallization/binding promoter is used to enhance the formation of flowable, compactible micro-particulates. The crystallization/binding promoter can be selected from the group consisting of an alcohol, such as ethanol, polyvinylpyrrolidone and a combination thereof. The promoter can also be a surface active agent. Surface active agents can be added to feedstock used to form the matrix. Alternatively, polydextrose can be used as a promoter by inclusion in the feedstock. In one embodiment promoter and a pharmaceutical are combined with the shearform matrix.

The additive portion of the mixture preferably includes an active ingredient.

The shearform matrix can be prepared by flash flow processing feedstock which includes saccharide based material as a carrier component. Sucrose is a preferred carrier, and it can be combined with other saccharide based carrier components, such as dextrose, and sugar alcohols, such as sorbitol, mannitol, etc. The feedstock can also include a crystallization enhancer such as a surfactant, e.g., tweens, spans, etc.

In order to form the comestible unit, a medium compression force can be used without fear of disrupting the disintegratability of the unit. The compression force need not exceed ten (10) Strong Cobb Units ("SCU"), and preferably does not exceed medium compression forces of between six (6) and eight (8) SCU's. In some embodiments, a low compression force can also be used. In either event, tablets produced according to the invention can be made low density and easily disintegrated.

Another method of identifying the compression force required to mold uncured matrix in accordance with the present invention is by identifying the density resulting from compacting. The product of the present invention should be compacted to a density of not greater than about 1.2, and preferably not greater than about 0.8.

In a most preferred form of the invention, the active ingredient is an antacid and the crystallization/binding promoter is ethanol.

It has also been found that when calcium is included as an active ingredient, the release characteristics of the dosage unit are very favorable. As a matter of fact, the unit can actually be used as a calcium supplement because of its high calcium release characteristics.

In the case of pharmaceuticals, it has been found that the pharmaceuticals are not "tied-up" with the components of the dosage unit. Consequently, pharmaceuticals are made available to bio-systems for which they have been administered.

Another type of additive which can be used in the present invention is an effervescent disintegration agent. The term effervescent disintegration agent(s) includes compounds which evolve gas. The preferred effervescent agents evolve gas by means of chemical reactions which take place upon exposure of the effervescent disintegration agent to saliva in the mouth. The agent or agents can be included in several ways in the units of the present invention. First of all, the agents can be incorporated in the matrix by mixing with the feedstock prior to flash flow processing. Alternatively, the entire effervescent agent can be mixed with the shearform matrix after it has been produced by flash flow techniques. As yet a third possibility, one part of the agent can be included in the feedstock which is flash flow processed while the other part of the agent can be incorporated after flash flow processing. In any event, the effervescent disintegration agent provides for controlled and rapid disintegration of the tablet when placed in the mouth and provides for a positive organoleptic sensation by the effervescent action in the mouth. The texture, speed and sensation of disintegration can especially be adapted for use by children in combination with taking one or more of the medicaments contemplated for use in the present invention.

The present invention also includes a composition for delivering an active ingredient wherein the active ingredient is incorporated in a molded saccharide-based crystalline structure. The composition also includes the saccharide-based structure which has a bi-dimensionally stabilized crystalline sugar. The sugar is produced by forming a sugar crystalline frame from an outer portion of an amorphous shearform sugar mass, and subsequently converting the remaining portion of the mass to a substantially completely crystalline structure. The product is preferably monodispersed and is also preferably microcrystalline. For definitions relating to monodispersed and microcrystalline as well as other definitions relating to the composition aspects of the present invention, reference is made to parent U.S. application Ser. No. 08/133,669, filed Oct. 7, 1993, which is incorporated herein by reference. The shearform mass can also include an additive which is co-crystallized in a crystalline product. The amorphous shearform mass is substantially rod-shaped, and has two dimensions lying in a cross-sectional plane of the rod. The single dimension extends along a linear axis of the rod. Preferably, the monodispersed structurally stabilized cross-section does not exceed 50 μm, and preferably does not exceed 10 μm.

Yet another manifestation of the present invention is a method of administering an active ingredient to a human host. The method includes ingesting a quick dissolve comestible unit prepared by the method of the present invention. The next step requires the host to retain the quick dissolve unit in the oral cavity for a time sufficient to contact the unit with water while in the oral cavity. Finally, the human host introduces water to the oral cavity, while the unit is retained therein, to enhance dissolution of the dosage unit.

As a result of the present invention, a quickly dispersable comestible unit can be manufactured for shipment and sales to consumers. The method of the present invention is such that the manufacturing can proceed on a continuous basis. Since the agglomerate can be compacted with medium compaction forces, a unit can be formed which is durable and can withstand handling associated with packaging and distribution.

Moreover, the dispersability of the unit is perceived as nearly instantaneous. Consequently, the consumer does not experience disagreeable effects of unpleasant ingredients lingering in the oral cavity.

These and other advantages of the present invention will be appreciated from the detailed description and examples which are set forth herein. The detailed description and the examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
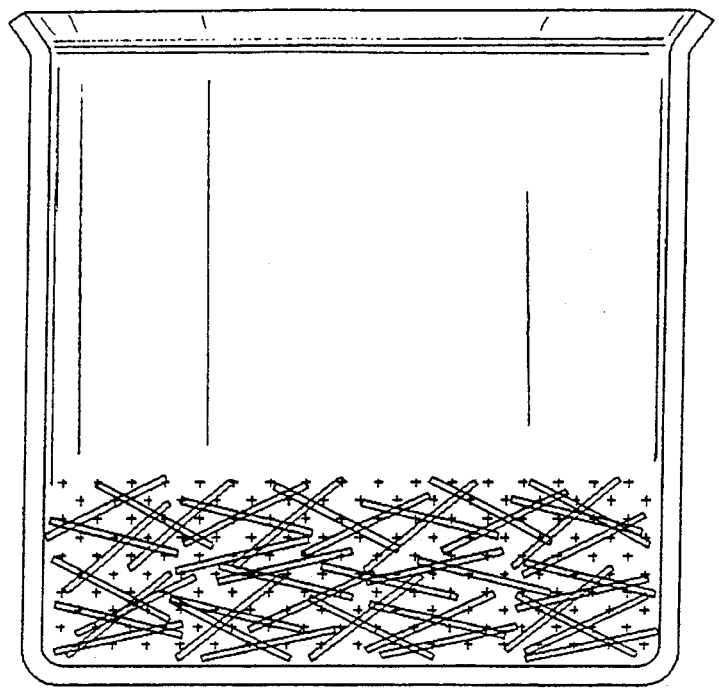
FIG. 1 is a schematic representation of the ingredients before forming flowable, compactible micro-particulates.

The present invention is a method of making comestible units which disintegrate quickly in the mouth of the consumer. The units produced in accordance with the present invention disintegrate nearly instantaneously. However, these units or tablets are capable of being manufactured so that they can be handled for packaging and distribution without deterioration of the integrity of the comestible units.

In the past, comestible units such as tablets have been made primarily by compressing feedstock under extremely high-pressure in order to provide the necessary hardness for handling required during packaging and distribution. Consequently, prior art tablets so produced are limited in that their high density reduces the capability of making them quickly disintegratable in the mouth. High density packing resulting from the high compression hinders the disintegration and wetting of the interior portion of the tablet. This aspect of the prior art has been improved by the technology disclosed in parent U.S. application Ser. No. 194,682, filed on Feb. 10, 1994. Similarly, another method of overcoming these and other difficulties has been disclosed in commonly-owned application bearing Attorney's Docket No. 447-105 which has been filed simultaneously herewith.

As a result of the present invention, however, a significant step forward has been made in the art of preparing comestible units which disintegrate very quickly in the mouth. In fact, tablets produced by the present invention disintegrate within seconds. The product is prepared by a unique combination of processing steps. The present invention also includes the product which is produced by the new process.

The first step of the procedure is to mix shearform matrix and an additive, such as an active ingredient. "Shearform matrix" in the present invention means a matrix produced by subjecting a feedstock which contains a carrier material to flash flow processing.

Flash flow processing can be accomplished several ways. Flash-heat and flash-shear are two processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. The force necessary to separate and discharge flowable feedstock is centrifugal force which is produced by the spinning head.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material until the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992 entitled "Process For Making Shearform Matrix," which is incorporated herein by reference.

The feedstock for producing shearform matrix includes a carrier material. The carrier material can be selected from material which is capable of undergoing both physical and/or chemical changes associated with flash-flow processing. Materials useful as matrices may be chosen from those carbohydrates which are capable of forming free-form agglomerates upon being processed.

Preferred carrier materials are chosen from such classes as sugars or sugar derivatives. "Sugars" are those substances which are based on simple crystalline mono- and di-saccharide structures, i.e., based on $C_5$ and $C_6$ sugar structures. "Sugars" include glucose, sucrose, maltose, lactose, arabinose, xylose, ribose, fructose, mannose, pentose, galactose sorbose, dextrose, sorbitol, xylitol, mannitol, pentatol, maltitol, isomalt, sucralose and mixtures thereof.

Preferred combinations of sugars includes sugars as used herein in combination with other mono-, di-, tri-, and polysaccharides up to 50% of the total amount, preferably up to 30%, and most preferably up to 20%.

A shearform product is used in the technique of the present invention to obtain the new sugar product. A shearform sugar product is a substantially amorphous sugar which results from subjecting sugar to heat and shear sufficient to transform crystalline (usually granulated) sugar to amorphous sugar without the use of a solution. Thus, in the sense of the present invention, a shearform sugar product is characterized as a sugar product resulting from a non-solubilized sugar. It is the starting material for forming the unique crystalline product of the present invention.

Other carrier materials can be used, but preferably in combination with sugar—not as a total replacement.

Maltodextrins are an example of other carrier materials. Maltodextrins include those mixtures of carbohydrates resulting from hydrolysis of a saccharide feedstock which are described as solids having a DE of up to and including 65.

The feedstock can also include maltooligosaccharides produced by selective hydrolysis of cornstarch followed by removal of high and low molecular weight compounds. The general description of maltooligosaccharides as contemplated herein is set forth in co-pending U.S. application Ser. No. 07/847,595 filed Mar. 5, 1992.

Polydextrose is also contemplated for use in combination with sugar in the carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of co-pending, U.S. application Ser. No. 07/881,612 filed May 12, 1992.

"Initiating crystallization" in the present invention means to induce crystallization. Shearform matrix used in the present invention contains a substantial amount of amorphous sugar. Crystallization can be initiated several ways. For example, crystallization promoters can be included in the feedstock used to make the shearform matrix. Crystallization promoters include surface active agents such as Tweens™, Spans™, and polydextrose, and mixtures thereof. Crystallization can also be initiated by adding a crystallization agent to the matrix before or after combining with an additive. Therefore, initiating crystallization in the present invention can occur before or after combining with the additive.

"Combining" an additive with shearform matrix to form flowable, compactible micro-particulates means to add and mix an additive before or after initiating crystallization to form a medium which consists of micro-particulates. Micro-particulates are discreet entities which appear to "roll" readily or "flow" in response to force of gravity and/or agitation. On a macroscopic scale micro-particulates appear as a flowable mass or medium. Consequently, the medium can be easily used in tabletting machinery without clogging and/or creation of undue dust in the ambient atmosphere.

The shearform matrix of the present invention is retrieved from processing, and generally "chopped" before combining with the additive. The additive can be any ingredient or ingredients needed to supply the comestible unit with the required characteristics. Preferably, the primary ingredient of the additive is an active ingredient which includes one or more medicinal substances.

Medicinal substances which can be used in the present invention are varied. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, antiuricemic drugs and mixtures thereof.

Especially preferred active ingredients contemplated for use in the present invention are antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include aspirin, acetaminophen, and acetaminophen plus caffeine.

Other preferred drugs for other preferred active ingredients for use in the present invention include antadiarrheals such as immodium AD, antihistamines, antitussives, decongestants, vitamins, and breath fresheners. Also contemplated for use herein are anxiolytics such as Xanax; antipsychotics such as clozaril and Haldol; non-steroidal anti-inflammatories (NSAID's) such as Voltaren and Lodine; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigraines such as Imigran, ACE-inhibitors such as Vasotec, Capoten and Zestril; Anti-Alzheimers agents, such as Nicergoline; and $Ca^H$-Antagonists such as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Other ingredients which may be included are fragrances, dyes, sweeteners both artificial and natural, and other additives.

For example, fillers may be used to increase the bulk of the tablet. Some of the commonly used fillers are calcium sulfate, both di- and tri basic, starch, calcium carbonate, microcrystalline cellulose, modified starches, lactose, sucrose, mannitol, and sorbitol.

Other materials which can be incorporated into the feedstock to enhance the shearform matrix include flavors and sweeteners (other than the carrier itself).

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Yet a further embodiment of the present invention includes the use of an effervescent disintegration agent. Its action can aid in the masking of objectionable taste of active ingredients such as vitamins, medicines and/or minerals, etc. It is generally believed that the positive organoleptic sensation achieved by the effervescent action in the mouth, the texture, speed and sensation of disintegration aids in masking undesirable flavor notes in the mouth.

In preferred embodiments of the present invention, the effervescent disintegration agent may include at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

Inasmuch as the term effervescent refers to those agents which evolve gas, the bubble or gas generating the action is most often the result of the reaction of a soluble acid source and an alkali metal carbonate or carbonate source. The reaction of these two general classes of compounds produces carbon dioxide gas upon contact with water included in saliva. Carbonate sources include dry solid carbonate and bicarbonate salts such as sodium bicarbonate, sodium carbonate, potassium bicarbonate and potassium carbonate, magnesium carbonate and sodium sesequicarbonate, sodium glycine carbonate, L-lysine carbonate, arginine carbonate and amorphous calcium carbonate. While the food acids can be those indicated above, acid anhydrides of the above-described acids may also be used. Acid salts may include sodium, dihydrogen phosphate, disodium dihydrogen pyrophosphate, acid citrate salts and sodium acid sulfite. Other source of effervescence can be included and the present invention is not limited to those specifically set forth herein.

Also as previously mentioned, the ingredients of the effervescent agent can be included in one of at least three different ways. The first method includes incorporating the entire effervescent agent in the feedstock which is used to form the shearform product. The second manner of incorporating an effervescent disintegrating agent is to include the entire agent as an additive which is mixed with shearform matrix after it is formed. The third method contemplates incorporating one portion of the disintegrating agent in the shearform matrix and another portion of the disintegrating agent as an additive after formation of the shearform matrix material. The artisan will determine the best way to preserve the agent for its disintegrative and effervescent properties upon ingestion by the host.

Crystallization can be enhanced by crystallization modifiers. Crystallization modifiers can be added to the feedstock before flash flow processing, such modifiers include, but are not limited to, surfactants (Spans™ and Tweens™), dextrose, polyethylene glycol (PEG), polypropylene glycol (PPG), etc. These modifiers generally provide controlled acceleration of crystallization while the matrix is bound.

Crystallization modifiers enhance the formation of a crystalline frame and the conversion of the remaining mass. Enhancement as used with respect to the process of the present invention principally means acceleration of the process. Enhancement also includes contribution to the strength of the crystalline structure, and predictability of results. Other benefits such as reduced-size product also is achieved by use of crystallization modifiers.

Crystallization modifiers, which are preferably added to sugars before being processed to amorphous shearform mass (or can be coated on the sugar), are used to affect the rate of crystallization. Water itself is a crystallization modifier, and is preferably included in the amorphous shearform sugar mass in an amount of between about 0.5% to about 2.0%. Non-saccharide hydrophilic organic materials (NSHMs) are also used as crystallization modifiers. Even though some NSHMs are surfactants, other materials can be used. Materials found to be most effective have a hydrophilic to lipid balance (HLB) of 6 or greater, i.e., they have the same degree of hydrophilicity as surfactants characterized by degree of HLB. Such materials include, but are not limited to anionic, cationic, zwitterionic surfactants as well as neutral materials which have an HLB of six (6) or greater. Preferred NSHMs are hydrophilic materials having polyethylene oxide linkages. Also, the preferred NSHM's have a molecular weight of at least 200 and preferably at least 400.

Lecithin is one surface active agent for use in the present invention. Lecithin can be included in the feedstock in an amount of from about 0.25 to about 2.00% by weight. Other surface active agents include, but are not limited to, the Spans™ and Tweens™ which are commercially available from ICI Americas Inc. Carbowax™ is yet another crystallization modifier which is very useful in the present invention. Preferably, Tweens™ or combinations of surface active agents are used to achieve the desired HLB.

By use of a surfactant the process and product of the present invention can be reproduced with a high degree of predictability. As additional crystallization modifiers which enhance the procedure and product of the present invention are identified, Applicants intend to include all such additional crystallization modifiers within the scope of the invention claimed herein.

Fillers may be used to increase the bulk of the tablet. Some of the commonly used fillers are calcium sulfate, both di- and tri basic, starch, calcium carbonate, microcrystalline cellulose, modified starches, lactose, sucrose, mannitol, and sorbitol.

Other ingredients includes binders which contribute to the ease of formation and general quality of the tablet. Binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Lubricants are also useful in tabletting formulations. Lubricants can include, but are not limited to, the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, dispersion enhancers can be used to enhance the breakability of the compressed tablet in an aqueous environment. The dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants. In view of the ease with which the product of the present invention disintegrates, there is little need for disintegrants.

The combination of shearform matrix and the additive must be provided as flavorable, compactible micro-particulates. The micro-particulates are agglomerates of a sort which include the ingredients of the mixture, but which are relatively low density. The "micro-particulates" of the present invention are capable of withstanding relatively high compaction force without experiencing an increase in density. The micro-particulates can then be compacted under relatively high compaction force to form a low density dosage unit having high structural integrity, strength and excellent appearance.

Micro-particulates are preferably formed by combining the mixture with a crystallization/binding promoter such as ethanol (preferably 200 proof), polyvinylpyrrolidone, a combination thereof, as well as other agents which enhance the formation of micro-particulates without increasing the density of the mixture.

The micro-particulates resulting from the above step can then be compacted, e.g, 6–8 SCUs, whereby a structurally strong tablet can be formed which has excellent appearance and can be handled without deterioration of the surface or structure.

"Compacting" in the present invention means to press into a comestible unit, e.g., a tablet, at a pressure generally greater than about 500 psi, but not necessarily as great as normal tabletting pressure, which are on the order of magnitude of thousands of psi (i.e., at least about 1000 psi). In one preferred embodiment wherein polydextrose (especially, Poly Dex™ brand polydextrose provided by A.E. Stanley & Co.) has been included as a crystallization promoter, compaction pressure as low as 50 psi has been found to be effective. In all cases herein, the micro-particulate medium being compacted includes shearform matrix which has been at least partially crystallized.

Other ingredients can also be used in the present invention either during the mixing stage, during the agglomeration stage, or after the agglomeration stage. Such ingredients are ingredients which are useful in tabletting such as glidants which adhere to cohesive material and enhance flow properties. Flow property is enhanced by reducing interparticle friction which otherwise exists. Glidants which can be used includes starch, talc, magnesium and calcium stearate, zinc stearate, dibasic calcium phosphate, magnesium carbonate, magnesium oxide, calcium silicate, and silica arogels.

Also color additives can be used in preparing tablets. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

As a result of the process of the present invention a strong, highly attractive tablet can be produced having a texture which is relatively open for ease of fracture and ease of solubilization. However, the unit remains high in strength because of the high-pressure of compacting each of the units.

In a preferred embodiment, the present invention is particularly useful for preparing antacid tablets. Antacids are conveniently provided in a chewable tablet form to provide a convenient method of delivering antacid to the consumer. The chewable form provides an advantage in that the tablet is broken up into granules during chewing and mixed with saliva before swallowing. This creates a suspension.

One of the disadvantages of current antacid tablets is that the mass of ingredients residing in the mouth during and after chewing have objectionable texture and taste. The present invention overcomes these disadvantages because of the rapid disintegration which occurs in the mouth. The objectionable texture and taste of disagreeable ingredients are reduced because the residence time in the mouth is substantially reduced.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

One method of measuring the results of the present invention is the ability to make a low density product. The micro-particulates are capable of being subjected to high-pressure without reducing the density of the resulting product. Accordingly, the product prepared in accordance with the present invention even after high-pressure-compaction will still remain below 1.2 grams per cubic centimeter (gr./cc), and preferably below 0.8 gr./cc.

The pressure required to prepare tablets in accordance with the present invention exceed those generally required in companion case (Attorney's Docket 447-105), but are less than those previously required with normal tabletting procedures (albeit some embodiments require no greater compaction pressure than that set forth in 447-105). As a result of the increase pressure which can be used to form tablets in accordance with the present invention, the strength of the product is increased, and the hardness of the surface is also increased. This results in a confection dosage unit which is able to be handled manually and machine processed without degradation of the surface or structural integrity.

Figure 2:
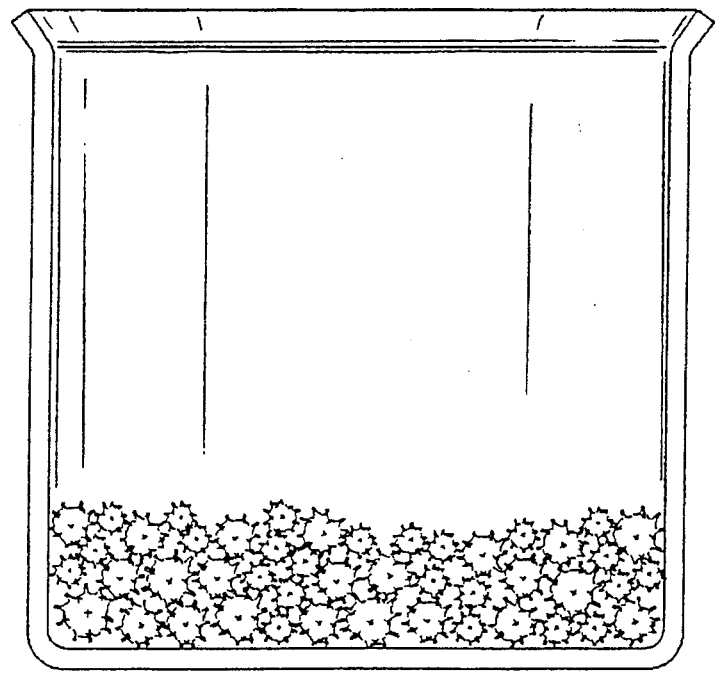
FIG. 2 is a schematic representation of micro-particulates formed from the mixture shown in FIG. 1.
Figure 3:
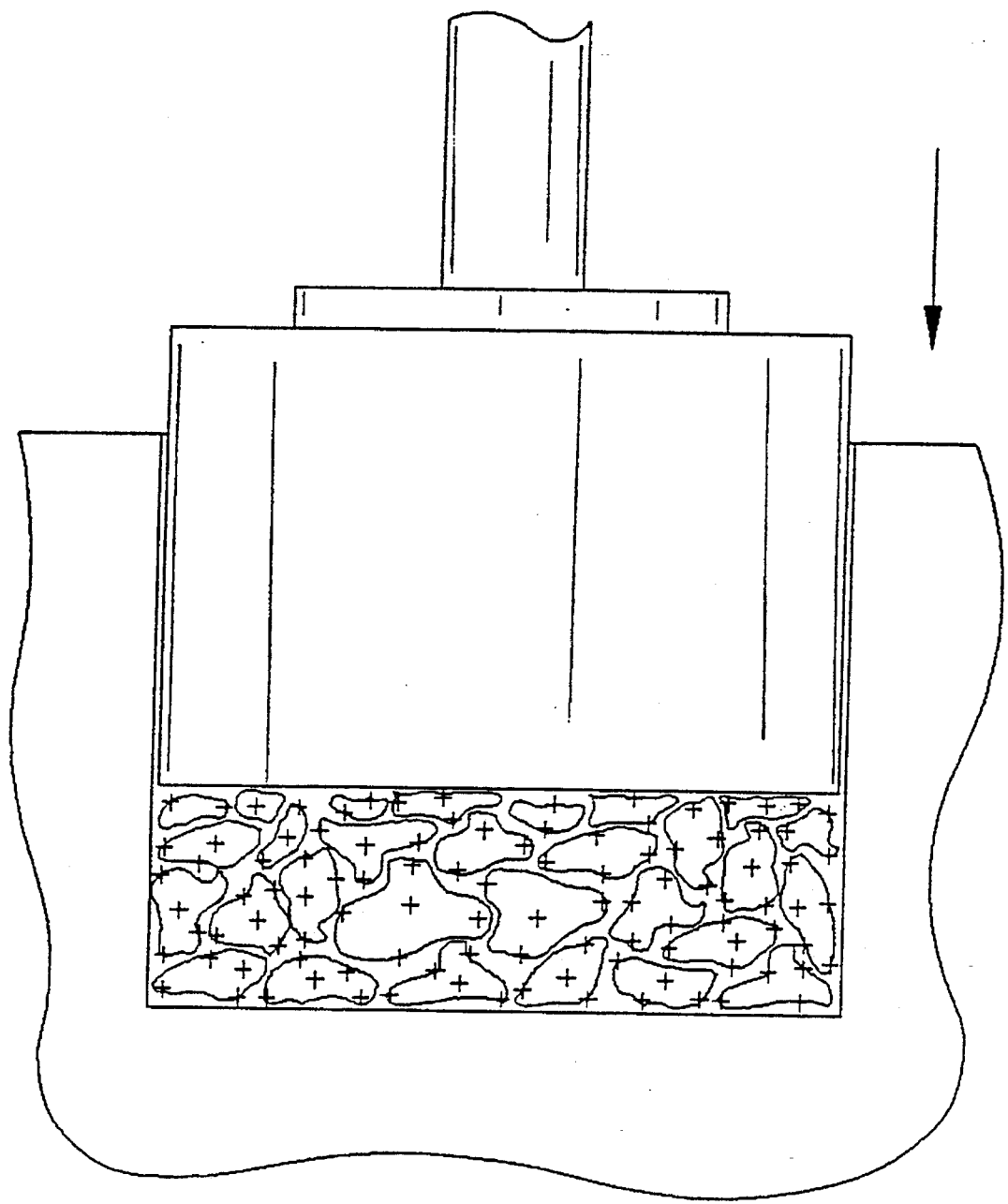
FIG. 3 is a schematic representation of compacting micro-particulates into a comestible unit in accordance with the invention.

Referring to FIGS. 1–3, the process of the present invention is described in greater detail. In FIG. 1, a combination of shearform matrix in the form of chopped floss material is depicted in mixture with a representative of an additive, i.e., +'s. An antacid agent is a preferred additive, +. In FIG. 1, the combination is shown as floss and additive particles indiscriminately mixed one with another. There is no fixed relationship between the particles in the mixture shown in FIG. 1. Crystallization of the floss is initiated either before or after the combination with an additive is formed.

In FIG. 2, the combination is shown as flowable, compactible micro-particulates. The micro-particulates shown in FIG. 2 are represented by collections of shearform matrix with the additive fixed therein and thereon. The transformation is enhanced when the combination shown in FIG. 1 is subjected to a crystallization/binding promoter such as ethanol, polyvinylpyrrolidone, or a combination thereof. Other crystallization/binding promoters may be used to form the micro-particulates. It is intended to include all such other agents useful for this purpose.

The micro-particulates form a medium which is flowable. Therefore, the medium is easily fed to dye cavities in tabletting apparatus without clogging moveable parts. Moreover, the incidence of dust is reduced.

Referring now to FIG. 3, a schematic representation has been made of the performance of the micro-particulates during actual compression. In FIG. 3, the micro-particulates are schematically represented under compaction force. The micro-particulates deform, but. their density is not increased. Basically, the spaces between micro-particulates are reduced or virtually eliminated, but the micro-particulates themselves retain their low density. Additive particles are retained in and on the surface of the agglomerates.

Micro-particulates retain their individual integrity and lines of disintegration are provided throughout the resulting unit. Moreover, since the mass can be subjected to relatively high-pressure-compaction, the surface of the resulting dosage unit is smooth, and the strength of the tablet is relatively high. Therefore, the resulting units can be easily handled without deterioration of the surface appearance or destruction of the comestible units.

In the formation of the micro-particulates the material preferably contains up to 5% water, and most preferably up to 1% water. The water can be provided by water contained in the ingredients such as that carried in the sugars or binders. Water can also be provided in small amounts in the alcohol, such as in 200 proof alcohol which absorbs moisture rapidly and generally contains small amounts of moisture, e.g., up to 1% by weight. The additional moisture can be provided by ambient surroundings such as the humidity in the air.

EXAMPLES

ANTACID EXAMPLE

Shearform matrixes were prepared for use in the process of the present invention. The matrixes were prepared by subjecting combinations of carrier material to flash flow processing in a cotton candy type apparatus. The combination included the saccharide-based carrier material sucrose, as well as other carriers, and surfactants such as Tween™ 80, which is supplied by ICI, and lecithin. The isomalt used herein is commonly available as Palatinit™ brand isomalt. The blends were provided according to the formulae set forth below in the Shearform Matrix Table.

| | SHEARFORM MATRIX TABLE | | | | | | |
|---|---|---|---|---|---|---|---|
| Ingredient | Matrix 1 | Matrix 2 | Matrix 3 | Matrix 4 | Matrix 5 | Matrix 6 | Matrix 7 |
| Sucrose (Granules) | 66.5% | 66.5% | 66.5% | 66.5% | 66.5% | — | — |
| Mannitol (Powdered) | 33.0% | 16.5% | 28.0% | 31.0% | 24.0% | — | — |
| Dextrose | — | 16.5% | 5.0% | — | — | — | 20.0% |
| Sorbitol | — | — | — | 2.0% | — | — | — |
| Surfactant | 0.5% | 0.5% | 0.5% | 0.5% | 0.5% | 1.4% | 1.4% |
| Isomalt | — | — | — | — | — | 95.6% | 20.0% |
| Maltitol | — | — | — | — | — | — | 55.6% |
| Polyglycerolesters | — | — | — | — | — | 3.0% | 3.0% |

The matrix recovered from each of the blends set forth above was a light colored floss, e.g., substantially white. Each matrix was then chopped for mixing with an additive, e.g., an antacid combination. The examples set forth hereinbelow refer to the matrices recovered from each of the blends above as M1, M2, . . . etc.

ANTACID EXAMPLE I

The first antacid example was mixed in accordance with the formula set forth below in Antacid Table I.

TABLE I

| ANTACID | |
|---|---|
| Ingredient | Percentage |
| Antacid Agent (CaCO$_3$) | 36.55% |
| M1 | 58.63% |
| Flavoring | 0.35% |
| Vegetable Oil | 0.50% |
| Flow Agent - | |
| Syloid 244 | 1.00% |
| Cab-O-Sil | 0.40% |

TABLE I-continued

| ANTACID | |
|---|---|
| Ingredient | Percentage |
| Starch | 2.00% |
| High Intensity Sweetener (Aspartame) | 0.07% |
| Lubricant (Mg Stearate) | 0.50% |
| | 100.00% |

The ingredients were combined by mixing to provide a mixture such as that shown in FIG. 1.

After the mixture was formed, ethanol (200 proof) was added and flowable compactible micro-particulates were formed. (About 4.0% of ethanol based on the weight of the mixture was used). The schematic representation of such agglomerates are shown in FIG. 2. After an agglomerate consistency was achieved, tablets were formed by compressing under a composition force of about 6 SCU. The weight of each tablet was about 1.500 grams.

The tablets so formed had an excellent appearance, and disintegrated immediately in the mouth of the consumer. The release capabilities of the calcium from the dosage unit has been set forth below in the Calcium Release Table. As can be seen from the release capabilities, not only is the dosage unit an excellent source of antacid agent, but can also be classified as a source of calcium for purposes of nutrition. Therefore, the dosage unit can be characterized as a nutritional calcium supplement.

ANTACID EXAMPLE II

A second example was prepared using the mixture set forth below in Antacid Table II.

TABLE II

| ANTACID | |
|---|---|
| Ingredient | Percentage |
| Antacid Agent (CaCO$_3$) | 36.55% |
| M2 | 58.86% |
| Peppermint Flavoring (Peppermint Oil) | 0.12% |
| Vegetable Oil | 0.50% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The above ingredients were mixed together and then subjected to agglomerating in the presence of ethanol (200 proof). Flowable, compactible micro-particulate were formed. (About 4% of ethanol based on the weight of the mixture was used).

The resulting agglomerate was directed to tabletting press and compressed at a compression force of about 6 SCU. The resulting tablets were smooth and had a high quality appearance. Furthermore, the product disintegrated immediately in the mouth of the consumer. Tests were also conducted on two of the samples to determine the release characteristics of the calcium. The results of the test are shown in the Release Table as tests results IIa and IIb.

ANTACID EXAMPLE III

Another example of an antacid dosage unit was prepared in accordance with the mixture set forth in Antacid Table III.

TABLE III

| ANTACID | |
|---|---|
| Ingredient | Percentage |
| Antacid Agent (CaCO$_3$) | 36.550% |
| M2 | 58.630% |
| Flavoring | 0.350% |
| Vegetable Oil | 0.500% |
| Flow Agent - | |
| Syloid 244 | 1.000% |
| Cab-O-Sil | 0.400% |
| Starch | 2.000% |
| High Intensity Sweetener (Aspartame) | 0.070% |
| Lubricant (Mg Stearate) | 0.500% |
| | 100.000% |

The ingredients set forth above were thoroughly mixed and flowable, compactible micro-particulates were formed. The agglomerates were formed in the presence of ethanol added in an amount sufficient to form the micro-particulate consistency (about 4% by weight of the total mixture). The ethanol was mixed thoroughly with the ingredients and the agglomeration formed.

The micro-particulate medium was then directed to a tablet forming press wherein tablets were prepared using a compaction pressure of about 6 SCU. The resulting tablets were at a high quality appearance, and were able to disintegrate immediately in the oral cavity.

Furthermore, the tablets prepared in accordance with this example were subjected to analysis for calcium release and the results have been set forth in the Calcium Release Table hereinbelow.

ANTACID EXAMPLE IV

Another antacid example was prepared in accordance with the formulation set forth in Antacid Table IV.

TABLE IV

| ANTACID | |
|---|---|
| Ingredient | Percentage |
| Antacid Agent (CaCO$_3$) | 36.55% |
| M2 | 58.59% |
| Flavoring | 0.35% |
| Vegetable Oil | 0.05% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| Red Coloring (FD&C No. 40) | 0.04% |
| | 100.00% |

The ingredients set forth above were thoroughly mixed until the homogenous red color appeared throughout the mixture. The mixture was then combined in the presence of ethanol (200 proof) in order to enhance formation of flowable, compactible micro-particulates. The micro-particulate medium was consistent in red color. The resulting agglomerates were tabletted using a compaction pressure of about 6 SCU.

The tablets formed therefrom had a good quality appearance including a consistent red color and a smooth surface. Furthermore, the tablets so prepared disintegrated immediately in the mouth of the consumer. The tablets prepared in accordance with the formulation set forth above were subjected to calcium release testing and the results have been set forth below in the Calcium Release Table.

ANTACID EXAMPLE V

Another antacid dosage unit was prepared in accordance with the formulation set forth below in Antacid Table V.

TABLE V

| ANTACID | |
| --- | --- |
| Ingredient | Percentage |
| Antacid Agent (CaCO$_3$) | 36.55% |
| M1 | 58.83% |
| Peppermint Flavoring (Peppermint Oil) | 0.15% |
| Vegetable Oil | 0.50% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The ingredients were blended thoroughly and then subjected to agglomeration by addition of ethanol while mixing. (The ethanol was added in an amount of about 4% by weight of the mixture).

The resulting flowable, compactible micro-particulate medium was then subjected to tabletting by compression in a tabletting unit at a compaction pressure of about 6 SCU. Each tablet weighed 1.500 grams.

The resulting tablets had a high quality appearance and disintegrated immediately in the oral cavity. Furthermore, the tablets were subjected to three separate tests to determine the calcium release characteristics. The results have been set forth in the Calcium Release Table as Va, Vb and Vc.

ANTACID EXAMPLE VI

A sixth antacid example was prepared using the formulation set forth below in Antacid Table VI.

TABLE VI

| ANTACID | |
| --- | --- |
| Ingredient | Percentage |
| Antacid Agent (CaCO$_3$) | 36.55% |
| M3 | 58.83% |
| Mint Flavor (Mint Blend) | 0.15% |
| Vegetable Oil | 0.50% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The ingredients set forth above were mixed until a homogeneous mixture was achieved. Flowable compactible micro-particulates were then formed by addition of ethanol (200 proof) and blended until the micro-particulate were formed. The micro-particulate agglomerates were then used to form tablets under compaction pressure of about 6 SCU.

The resulting tablets has an excellent taste and good appearance and were easily disintegrated in the mouth of the consumer. Calcium release tests were performed on the tablets and the results have been reported in the Calcium Release Table set forth below.

ANTACID EXAMPLE VII

A seventh antacid dosage unit was prepared in accordance with the formulation set forth in Antacid Table VII.

TABLE VII

| ANTACID | |
| --- | --- |
| Ingredient | Percentage |
| Antacid Agent (CaCO$_3$) | 36.55% |
| M4 | 58.73% |
| Flavor | 0.25% |
| Vegetable Oil | 0.50% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The ingredients were blended and agglomerated to form flowable, compactible micro-particulates by use of 200 proof ethanol. The resulting micro-particulate medium was subjected to tabletting and the tablet press had a compaction pressure of about 6 SCU.

The resulting tablets had a smooth surface, excellent appearance and structural integrity. Moreover, the tablets disintegrated immediately in the mouth of the consumer. The calcium release characteristics were also excellent and have been reported herein in the Calcium Release Table.

ANTACID EXAMPLE VIII

Another antacid example was prepared using the formulation set forth below in Antacid Table VIII.

TABLE VIII

| ANTACID | |
| --- | --- |
| Ingredient | Percentage |
| Antacid Agent - | |
| CaCO$_3$ | 29.50% |
| Mg(OH)$_2$ | 5.79% |
| M1 | 59.99% |
| Flavoring | 0.35% |
| Vegetable Oil | 0.50% |
| Flow Agent - Syloid 244 | 1.00% |
| Starch | 2.00% |
| High Intensity Sweetener (Aspartame) | 0.07% |
| Lubricant (Mg Stearate) | 0.50% |
| Crystallization/Binding Promoter (Polyvinylpyrrolidone) | 0.30% |
| | 100.00% |

The above ingredients were combined and then subjected to agglomeration by adding ethanol (200 proof) and mixing until a flowable, compactible micro-particulate medium was formed. It is noted that polyvinylpyrrolidone and ethanol were combined in the present mixture as a crystallization/ binding promoter. Polyvinylpyrrolidone is included as an ingredient in Antacid Table VIII. Ethanol was added after the mixture was formed in an amount of about 4% by weight of the total mixture.

The resulting micro-particulate medium was subjected to tabletting under compaction pressure of about 6 SCU. The resulting tablets had excellent appearance, a good surface and high structurally integrity. Furthermore, the tablets disintegrated immediately in the mouth of the consumer. The calcium release characteristics have been set forth below in the Calcium Release Table.

ANTACID EXAMPLE IX

Another antacid example was prepared using the formulation set forth below.

TABLE IX

| ANTACID | |
|---|---|
| Ingredient | Percentage |
| Antacid Agent - | |
| $CaCO_3$ | 29.50% |
| $Mg(OH)_2$ | 5.79% |
| M2 | 60.12% |
| Peppermint Flavor (Peppermint Oil) | 0.12% |
| Vegetable Oil | 0.50% |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The ingredients were mixed and subjected to agglomeration to form a flowable, compactible micro-particulate medium in the presence of 200 proof ethanol. The ethanol was added and mixed with the ingredients to form the agglomeration.

The resulting agglomerate was subjected to a tabletting force of about 6 SCU. The resulting tablets had excellent appearance and a high structural integrity and good surface qualities. The tablets disintegrated immediately in the mouth of the consumer. Furthermore, the tablets were subjected to calcium release and were shown to have excellent calcium release characteristics. The results are set fourth in the Calcium Release Table below.

ANTACID EXAMPLE X

Another antacid example was prepared using the formulation set forth below.

TABLE X

| ANTACID | |
|---|---|
| Ingredient | Percentage |
| Antacid Agent - | |
| $CaCO_3$ | 29.50% |
| $Mg(OH)_2$ | 5.79% |
| M1 | 59.89% |
| Flavoring | 0.35% |
| Vegetable Oil | 0.50% |

TABLE X-continued

| ANTACID | |
|---|---|
| Ingredient | Percentage |
| Flow Agent - | |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| Red Coloring (FD&C No. 40) | 0.04% |
| | 100.00% |

The above ingredients were thoroughly mixed and then agglomerated by use of 200 proof ethanol in an amount of about 4% by weight of the total mixture. The resulting micro-particulate medium was subjected to tablet formation under a compaction force of about 6 SCU.

The resulting tablets had a uniform red surface appearance and good structural integrity. Furthermore, the tablets disintegrated immediately in the mouth of the consumer. The tablets were then subjected to calcium release tests and the results have been reported herein in the Calcium Release Table.

CALCIUM RELEASE CHARACTERISTICS

An assay was conducted in order to determine the calcium release characteristics of the samples prepared as set forth above. The calcium release characteristics were prepared in accordance with the protocol set forth in the United States Pharmacopeia.

Several tablets were weighed and powdered, and the weight of each of the samples tested had a dosage amount of 550 mg. This powder was introduced to water to which 10 mm. of 1N HCl had been added. This was boiled for 30 minutes, allowed to cool, and then transferred to a 100 mL volumetric flask with the aid of water. This was diluted with water to volume, mixed, and filtered. Twenty (20) mL. of the filtrate was transferred to a suitable container and diluted with water to 100 mL. Fifteen (15) mL. of 1N NaOH was added along with 5 mL. of triethanolamine, and 100 mg. of hydroxy naphthol blue trituration, and titrated with 0.05M of disodium ethylenediamine-tetraacetate VS until the solution is a deep blue color. Each mL. of 0.05 disodium ethylenediamine-tetraacetate is equivalent to 5.004 mg. of calcium carbonate ($CaCo_3$). The results of the assay have been set forth below in the Calcium Release Table.

| CALCIUM RELEASE TABLE | |
|---|---|
| Sample | % Calcium Release |
| I. | 95.76 |
| IIa. | 95.21 |
| IIb. | 95.76 |
| III. | 95.48 |
| IV. | 94.93 |
| Va. | 96.03 |
| Vb. | 93.58 |
| Vc. | 96.03 |
| VI. | 94.47 |
| VII. | 87.41 |
| VIII. | 98.64 |
| IX. | 95.25 |
| X. | 94.92 |

As can be seen, the calcium released at 30 minutes was excellent on all the samples prepared in accordance with the present invention.

ACETAMINOPHEN EXAMPLES

Several examples were prepared using the active ingredient acetaminophen (APAP). Acetaminophen is well known to have a disagreeable impact in the oral cavity. Thus, it is desirable to provide a comestible for delivering acetaminophen which masks the taste and which minimizes the time the ingredients reside in the mouth. Therefore, these examples were prepared with acetaminophen. All the examples were prepared using the floss formulation M1. One additional example was prepared with aspirin.

ACETAMINOPHEN EXAMPLE XI

An acetaminophen example was prepared using the formulation set forth in Acetaminophen Table XI.

TABLE XI

| ACETAMINOPHEN | |
| --- | --- |
| Ingredient | Percentage |
| M1 | 74.305% |
| Acetaminophen (APAP) | 21.660% |
| APAP Mask | 0.160% |
| High Intensity Sweetener | 1.300% |
| Grape Flavor | 0.500% |
| Hydrol 92 | 2.000% |
| Blue Coloring | 0.042% |
| Red Coloring | 0.033% |
| | 100.000% |

The above formulation was blended and then subjected to treatment with a crystallization/binding promoter, i.e., 20% of a 0.5% PVP solution (PVP K-30) in 200 proof ethanol. About 20 ml of the crystallization/binding promoter was added and combined with the ingredients. A flowable, compactible micro-particulate medium was formed. The medium were then subjected to tabletting under a compaction pressure of about 6 SCU.

The resulting tablets disintegrated quickly in the mouth. The disagreeable impact of acetaminophen in the mouth was significantly reduced. Furthermore, the release of the acetaminophen is expected to be quite efficient, especially in view of the high release characteristics as reported above in the Calcium Release Table.

ACETAMINOPHEN EXAMPLE XII

Another example was prepared in accordance with the formula set forth in Acetaminophen Table XII.

TABLE XII

| ACETAMINOPHEN | |
| --- | --- |
| Ingredient | Percentage |
| M2 | 69.05% |
| Acetaminophen (APAP) | 25.00% |
| APAP Mask | 0.25% |
| Yellow Coloring (HT Aluminum Lake) | 0.15% |
| Hydrol 92 | 2.00% |
| High Intensity Sweetener | 0.80% |
| Flavoring | 2.25% |
| | 100.50% |

The above ingredients were mixed and then subjected to formation of flowable, compactible micro-particulates in the presence of 200 proof ethanol having added thereto 20% of a 0.5% PVP solution. The micro-particulates medium was subjected to tabletting under a pressure of about 6 SCU. The resulting tablets quickly disintegrated in the oral cavity. They had excellent structural integrity and appearance.

Moreover, they were expected to provide excellent acetaminophen release characteristics.

ACETAMINOPHEN EXAMPLE XIII

Another example was prepared using acetaminophen as the active ingredient in accordance with the formula set forth below in Acetaminophen Table XIII.

TABLE XIII

| ACETAMINOPHEN | |
| --- | --- |
| Ingredient | Percentage |
| M1 | 74.22% |
| Acetaminophen (APAP) | 16.25% |
| APAP Mask | 0.25% |
| Caffeine | 3.25% |
| Caffeine Mask | 0.25% |
| Hydrol 92 | 2.00% |
| Red Color | 0.08% |
| Flavor | 2.40% |
| High Intensity Sweetener | 1.30% |
| | 100.00% |

The above formulation was blended and then agglomerated using a 10% ethanol solution. The resulting agglomerate was tabletted under 35 pounds of pressure in a 15/16 inch die.

The resulting tablet was a lightweight tablet which disintegrated quickly in the mouth. The flavor was palatable in spite of the presence of the highly objectionable acetaminophen.

The appearance of the tablet was excellent, and the release of the acetaminophen is expected to be quite excellent.

MULTI-VITAMIN EXAMPLE XIV

One example has been prepared for a multi-vitamin dosage unit. The matrix was a lactose matrix prepared in accordance with the following formulation.

| MATRIX XIV | | |
| --- | --- | --- |
| Ingredient | Percent % | Weight |
| Sucrose | 59.35% | 356.10 |
| Dextrose | 18.00% | 108.00 |
| Mannitol | 20.00% | 120.00 |
| Lactose | 2.00% | 12.00 |
| Surfactant (Tween 80) | 0.25% | 2.40 |
| Polydextrose | 0.40% | 2.40 |
| | 100.00% | 600.00 g |

The ingredients were subject to flash flow processing by use of a flash heat, i.e., subjected to spinning in a cotton candy type machine at about 3600 r.p.m. The resulting product was a floss which was chopped in preparation for combining with additives.

A micro-particulate medium was prepared in accordance with the process of the present invention based on the formulation set forth below:

TABLE XIV

MULTI-VITAMIN

| Ingredient | Percentage |
| --- | --- |
| Matrix XIV | 55.685% |
| High Intensity Sweetener | 0.450% |
| Sweetener Mask | 0.200% |
| Starch | 2.000% |
| Coloring | 0.250% |
| Oleaginous | 0.500% |
| Flow Agent | 1.400% |
| Flavor | 3.500% |
| Lubricant | 0.750% |
| Multi-Vitamin Component | |
| Vitamin A | 1.778% |
| Vitamin D3 | 0.867% |
| Vitamin E | 1.913% |
| Vitamin B1 | 0.084% |
| Vitamin B2 | 0.138% |
| Vitamin B6 | 0.103% |
| Vitamin B12 | 0.092% |
| Vitamin C | 4.792% |
| Bioten | 0.250% |
| Folic Acid | 0.738% |
| Nicotinamide | 1.100% |
| Pantothenic Acid | 1.163% |
| Calcium Carbonate | 6.427% |
| Magnesium Oxide | 0.067% |
| Phosphorous | 14.655% |
| Iron | 0.570% |
| Zinc | 0.430% |
| Manganese | 0.046% |
| Copper | 0.052% |
| | 100.000% |

The above ingredients were combined and mixed in the presence of 200 proof ethanol, which was added in an amount of 4% based on the weight of the mixture. As a result of the above procedure, a flowable, compactible micro-particulate medium was formed.

The medium was then directed to a tabletting machine and tabletted under a compaction pressure of only 35 SCUs to provide a very attractive tablet which has excellent dispersability in the oral cavity. Moreover, the otherwise objectionable taste generally associated with vitamins and minerals, was overcome to the extent that the product was suitable for human consumption.

MICRO-PARTICULATE EXAMPLES

The micro-particulate medium formed as a result of the present invention demonstrates excellent flowability and handling capabilities for use in tabletting. The micro-particulates are of very small size and yet retain flowable characteristics, that is to say they "roll" easily in the medium. In the past, it has been a laborious task to obtain small particulates which are flowable for purposes of tabletting. Granulation methods known in the art produce a high quantity of dust as a by-product of grinding which is required to obtain the small particle size.

As a consequence of the present invention, the micro-particulate medium can be produced with little or no dust, and yet retain excellent flow characteristics.

To demonstrate this characteristic, two formulas were prepared and a sieve analysis was performed. The media were prepared in accordance with the formulas set forth below in the Sieve Analysis Formulation Table. The matrix used for each of the examples, i.e., Sieve XV and Sieve XVI, was of the type set forth in the Antacid Examples, especially M2 and M3.

SIEVE ANALYSIS FORMULATION TABLE

| Ingredient | Sieve XV | Sieve XVI |
| --- | --- | --- |
| Matrix | 58.53% | 58.90% |
| CaCO₃ | 36.55% | 36.55% |
| High Intensity Sweetener | 0.07% | — |
| Flavor | 0.35% | 0.15% |
| Vegetable Oil | 0.50% | 0.50% |
| Flow Agent | 1.40% | 1.40% |
| Starch | 2.00% | 2.00% |
| Color | 0.10% | — |
| Lubricant | 0.50% | 0.50% |
| | 100.00% | 100.00 |

The ingredients were prepared in accordance with the present invention and a sieve analysis was performed to determine the size of the micro-particulates which compose the mediums. The results of the sieve analysis have been set forth below in the Sieve Analysis Table.

SIEVE ANALYSIS TABLE

| Sieve Size | *Sieve XV | *Sieve XVI |
| --- | --- | --- |
| 10 | 5.380% | 4.415% |
| 20 | 7.475% | 5.660% |
| 40 | 5.185% | 5.535% |
| 60 | 4.230% | 5.560% |
| 80 | 4.610% | 4.635% |
| 100 | 13.465% | 6.605% |
| Pan | 59.655% | 67.590% |

*Percentages represents amount retained on Sieve.

Bearing in mind that the higher the sieve number the smaller the opening, it should be noted that 75–85% pass through a 60 or greater mesh sieve. These micro-particulates are very small size but are excellent for tabletting. Moreover, the tablets produced therefrom result in excellent disintegration and texture. These tablets overcome the well-known difficulty of retaining a grainy texture in the mouth.

In order to emphasize the fineness of the micro-particulates which make up the tabletting medium, it should be noted that a 60 size sieve is no greater than a 250 micro-particle. Thus, 75–85% of the micro-particulates are less than only 250 μm. 59–67% of the micro-particulates are less than 150 μm, which is the opening provided by a sieve of 100.

These results are quite unexpected since it has not been possible to produce an excellent disintegrating and textured tablet using a dry micro-particulate medium having substantially no free moisture and in the absence of heat.

Thus, while there had been described what are presently believed to be the preferred embodiments of the present invention, those skilled in the art will appreciate that other and further embodiments can be made without departing from the spirit of the invention and it is intended to include all such further modifications and changes as come within the true scope of the claims as set forth herein.

What is claimed is:

1. A comestible unit which disperses quickly in the mouth prepared from the process comprising:

a) subjecting to flash-flow processing a feedstock comprising a carbohydrate capable of undergoing flash-flow processing without use of a solution to provide a shearform matrix:

b) initiating crystallization of said shear/form matrix:

c) forming flowable compactible micro-particulates by combining an additive with said shearform matrix; and d) compacting said micro-particulates resulting from step "c," which comprises at least partially crystallized shearform matrix, to form said unit.

2. The unit according to claim 1, wherein said combining further comprises subjecting said additive and said matrix to treatment with a crystallization/binding promotor.

3. The unit according to claim 2, wherein said promoter comprises an ingredient selected from the group consisting of an alcohol, polyvinylpyrrolidone, and a mixture thereof.

4. The unit according to claim 1, wherein a crystallization/binding promoter is incorporated in said shearform matrix by including said promoter in feedstock from which said matrix is formed.

5. The unit according to claim 4, wherein said promoter is a surface active agent.

6. The unit according to claim 4, wherein said promoter is polydextrose.

7. The unit according to claim 1, wherein said additive is an active ingredient.

8. The unit according to claim 7, wherein said active ingredient is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

9. The unit according to claim 7, wherein said active is ibuprofen.

10. The unit according to claim 7, wherein said active ingredient is acetaminophen.

11. The active ingredient according to claim 7, wherein said active ingredient is aspirin.

12. The unit according to claim 7, wherein said active ingredient is an $H_2$ antagonist.

13. The unit according to claim 7, wherein said active ingredient is an antacid.

14. The unit according to claim 7, wherein said active ingredient is a breath freshener.

15. The unit according to claim 1, wherein said additive is a pharmaceutical and said combining further comprises subjecting said additive and said matrix to treatment with a crystallization/binding promoter.

16. The unit according to claim 1, which further comprises an effervescent disintegration agent.

17. A composition for delivering an active ingredient comprising:

an active ingredient; and a saccharide-based crystalline structure comprising a bi-dimensionally continuously bound and stabilized crystalline sugar produced by i) initiating formation of a sugar crystalline frame from an outer portion of amorphous shearform sugar masses, ii) forming flowable compactible micro-particulates by combining said active ingredient with said shearform matrix to;

iii) compacting said masses to form a unit dosage, and iv) subsequently converting the remaining portion of said masses to a substantially completely crystalline structure which is continuously bound and stabilized, whereby said active ingredient is incorporated in said saccharide-based crystalline structure.

18. The composition of claim 17, wherein said masses are bi-dimensionally monodispersed.

19. The composition of claim 17, wherein said shearform masses further comprise an additive whereby said additive is co-crystallized in said crystalline product.

20. The composition of claim 18, wherein said monodispersed stabilized masses are microcrystalline.

21. The composition of claim 18, wherein said amorphous shearform product is substantially rod shaped, said two dimensions lying in a cross-sectional plane of said rod and a third dimension extends along the linear axis of said rod.

22. The composition of claim 21, wherein the monodispersed structurally stabilized cross-section does not exceed 50 µm.

23. The composition of claim 22, wherein said cross-section does not exceed 10 µm.

* * * * *